United States Patent [19]

van Leerdam

[11] Patent Number: 4,578,074

[45] Date of Patent: Mar. 25, 1986

[54] INFUSION LIQUID POUCH

[75] Inventor: Hans M. L. van Leerdam, Berkhout, Netherlands

[73] Assignee: Medistad Holland V.V., Medemblik, Netherlands

[21] Appl. No.: 514,472

[22] Filed: Jul. 18, 1983

[30] Foreign Application Priority Data

Jul. 22, 1982 [NL] Netherlands ........................ 8202952

[51] Int. Cl.⁴ ........................ A61B 19/00; B65B 7/02; B65D 33/16; B65D 33/36

[52] U.S. Cl. .................................... 604/408; 604/415; 383/66; 156/69

[58] Field of Search ..................... 156/69, 242, 244.18, 156/244.19, 250, 293, 294, 308.2; 604/408, 415, 262, 409, 410; 215/247, 249; 383/41, 43, 59, 96, 66, 55, 60; 53/469, 471, 273; 206/0.5, 219; 128/DIG. 24; 141/314, 316, 329, 330

[56] References Cited

U.S. PATENT DOCUMENTS

| | | | |
|---|---|---|---|
| 3,030,955 | 4/1962 | Gossett et al. | 604/408 |
| 3,509,879 | 5/1970 | Bathish et al. | 604/408 |
| 3,994,412 | 11/1976 | Difiglio | 604/408 X |
| 4,227,954 | 10/1980 | Ward et al. | 156/250 |
| 4,410,026 | 10/1983 | Boggs et al. | 604/408 X |

FOREIGN PATENT DOCUMENTS

| | | | |
|---|---|---|---|
| 1144814 | 10/1957 | France | 604/408 |
| 0110204 | 12/1964 | Netherlands | 604/408 |
| 1579065 | 11/1980 | United Kingdom | 604/408 |

*Primary Examiner*—Edward Kimlin
*Assistant Examiner*—Ramon R. Hoch
*Attorney, Agent, or Firm*—Beehler, Pavitt, Siegemund, Jagger, & Martella

[57] ABSTRACT

A closed pouch for infusion liquid is made from a continuously extruded plastics hose by providing transverse seals and cutting the hose in said seals, and an assembly of two necks and a filling hose connection is secured to the outer wall of each pouch, said wall being pierced when liquid is to be extracted from or supplied to the pouch through one of said necks. Such an assembly is made from plastics as a unitary structure together with closing caps for the necks and a common flange to be secured to said wall. One neck is provided, at the flange side, with an enlarged bore terminating in a shoulder which is substantially parallel to the flange, and a pierceable sealing pad is inserted from the flange side into said enlarged bore, the latter being eventually closed by the pouch wall.

9 Claims, 4 Drawing Figures

INFUSION LIQUID POUCH

Figure 1:
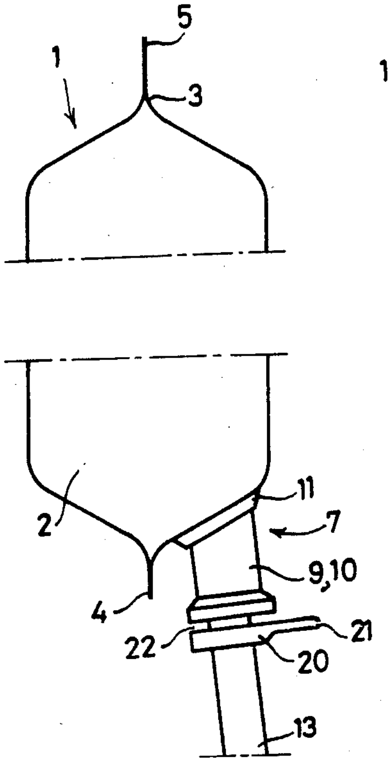

Infusion liquid pouches made of flexible plastics are known in several forms. Such a pouch comprises a first hollow neck closed by a removable cap, the bore of said neck being adapted for sealingly receiving a hollow plastics spike which is connected, by means of a flexible tube, to an infusion needle, a second similar neck being provided, moreover, with a pad made of rubber or the like arranged in an enlarged bore portion and adapted to be pierced by the thin steel needle of an injection syringe, in order to enable to add to the infusion liquid in the pouch a metered amount of a medicament or other auxiliary substance, which pad will sufficiently seal the opening after retracting the needle. Furthermore a flexible filling tube is generally provided by means of which the pouch can be filled, and which is closed in a sterile manner by fusing after filling the container.

In some known pouches of this kind the necks and the filling tube are incorporated in a seal interconnecting two walls of the pouch. Making such a seal with the necks incorporated therein is, however, onerous, and requires additional precautions for keeping the interior of the pouch free from contaminants.

From U.S. Pat. No. 3,030,955 (Gossett) an infusion liquid pouch is known which is formed from an extruded plastics hose divided by means of transverse seals into separate parts, and by cutting said seals separate and completely closed pouches are obtained. These pouches are internally substantially free from contaminants since the hose can be blown by means of clean air, and because of the relatively high formation temperature a primary sterilisation of the pouches will already be obtained. To this pouch necks are welded or glued, the pouch wall closing said necks at the inner side, so that, when inserting a spike or needle, this wall is to be pierced. The necks are, in particular, directed at an angle with the pouch wall so that, when inserting a spike or needle, the opposing panel wall cannot be touched.

A disadvantage of this known infusion pouch is that the necks are to be separately manufactured and secured, and are to be separately provided with closing caps too, and in the second neck the pierceable pad is to be retained by means of rigid sleeves which must be forced into the neck bore, which must be done from the outer side so that the associated closing cap should be separately provided. This is very complicated and time consuming, which is an obstacle to the automatization of the assembling of such pouches, and unfavourably influences the price thereof.

There exists a need for very cheap infusion pouches, and, therefore, for a method allowing a complete automatization of the manufacture thereof.

The invention provides such a method which is characterised in that both necks and associated closing caps as well as the filling tube connection are produced as a unitary structure made of plastics with a common flange, the second neck being provided, at its flange side, with an enlarged bore portion with a shoulder substantially parallel to said flange, the pierceable pad being pressed under some compression thereof into said bore portion and against said shoulder, the whole assembly then being positioned with said flange on a lateral wall of a pouch, which flange is, finally, secured on the pouch wall.

Inserting the pierceable pad can be done automatically in a simple manner, since this is done transversely to the flange surface and over a small depth, and, moreover, a high clamping force is not required, and the pad should only be elastically compressed so far as is required for closing a needle hole. Moreover the neck assembly is secured to a pouch immediately thereafter so that the pad will be sufficiently protected and retained by the wall of said pouch. Also positioning and securing said assembly can be done automatically in a simple and rapid manner, since the necks form a unitary structure with the common flange, and no additional operations are required for providing the closing caps.

From U.S. Pat. No. 3,509,879 (Bathish) a blood transfusion pouch is known per se, in which two necks of a different diameter, each designed for receiving a hollow plastics spike, as well as a filling tube are connected to a flange made of a plastics material, which flange is secured to a plane piece of plastics foil, the latter being folded in the region of said necks and then being sealed along three edges so as to form a closed pouch provided with necks. A disadvantage thereof is that the plastics foil, at the side which is to form the inner surface of the pouch, can be contaminated, and sealing around the pouch is time consuming. Moreover the closing caps are to be separately arranged.

In particular, before arranging the assembly of the invention, an incision in the pouch wall in the point where the filling tube connection is to be positioned, which is, in particular, cross-shaped, is made by means of a cutting knife with accurately adjustable cutting depth so that, after providing the neck assembly, the interior of the filling tube will directly communicate with the interior of the pouch.

For inserting the pierceable pad the assembly can be supported in a suitable jig on the flange surface opposite to the connection surface, said jig being adapted to take up the insertion force which is directed substantially perpendicularly to said surface.

The invention relates, furthermore, to an infusion pouch manufactured from a plastics foil hose by means of this method, said pouch comprising hollow necks each closed by a removable cap, one neck being adapted for receiving a hollow spike, and the other one being provided with a pad adapted to be pierced by a hollow needle and to close again the needle hole after retracting said needle, and further comprising a filling tube connection, which pouch is characterised in that said necks, caps, filling hose connection and a common flange form a unitary structure connected to a lateral wall of the pouch, the second neck being provided with an enlarged bore portion beginning at the flange side and terminating at a shoulder which is substantially parallel to the flange surface, said pad being enclosed in said enlarged bore portion between said shoulder and the adjoining pouch wall.

Said necks and tube connection are, in particular, interconnected by means of a relatively stiff connecting ridge forming a part of said unitary structure, so as to make the latter more rigid, which is, in particular, favourable when removing the closing caps and inserting a spike or needle, and provides a better grip thereon.

The filling tube connection can comprise, in particular, a stepped bore so as to accommodate filling tubes of different diameters, and said connection can also be made in the form of a sealed tube section to which an extension tube can be welded.

The first neck is preferably provided with internal ripples so as to provide a better grip on an inserted spike.

The pouch wall can be provided with a throughgoing incision below the tube connection providing a communication between said connection and the interior of the pouch.

Figure 2:
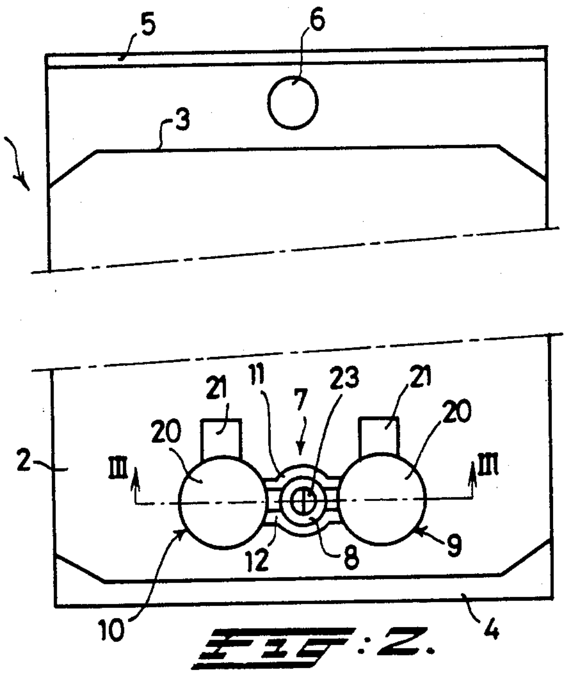
Figure 4:
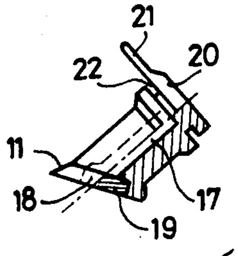
Figure 3:
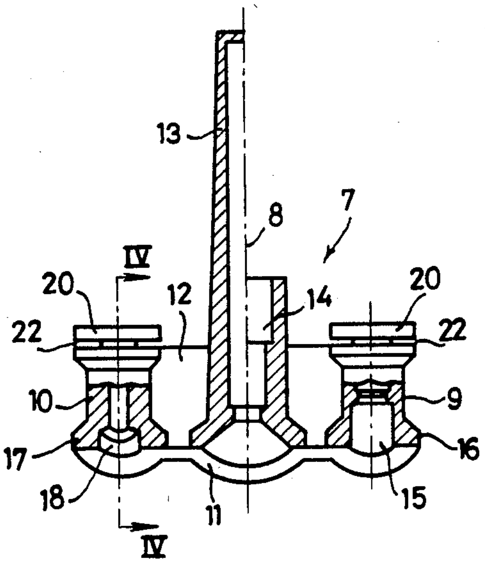

The invention will be elucidated below in more detail by reference to a drawing, showing in:

FIGS. 1 and 2 two views of a pouch provided with a connection assembly according to the invention;

FIG. 3 partial cross-sections on the line III—III of FIG. 2 of two embodiments of an assembly according to the invention without a pouch wall; and FIG. 4 a partial side view, partly in section on the line IV—IV of FIG. 3.

In FIGS. 1 and 2 an infusion pouch 1 is shown consisting of a wall 2 formed by a piece of plastics foil sealed at 3 and 4. Another seal at the upper side forms an additional reinforcement above a suspension eye 6.

At one side of the pouch 1 a connection assembly 7 is secured to the wall 2. This assembly is produced by injection moulding, and consists, in particular, of the same plastics material as the wall 2, so that, then, a connection between both can be made by means of a solvent. In the case of plastics which cannot be interconnected in this manner, a suitable glue or welding connection can be used.

This assembly 7 comprises, in the case shown, a tube connection spout 8 and two necks 9 and 10 which are interconnected by means of a common flange 11 and a connecting ridge 12, which flange is to be secured on the pouch wall 2. The spout 8 is a connector for a flexible filling tube 13. The latter tube can be continuous with said spout as shown in the left-hand part of FIG. 3, but can also be glued or welded in the spout 8 and, in particular, the latter can be provided with a stepped bore 14 for different tube widths as shown in the right-hand part of FIG. 3.

In the case of a continuous tube the latter can be closed at its free extremity so as to obtain a sterile closure. After cutting off the closed extremity, a sterile connection with a filling tube can be made.

The neck 9 is intended for drawing-off liquid from the pouch 1, and is designed for inserting therein a hollow pin or socalled spike made of plastics, the neck portion of which closely fits into the bore 15 of the neck 9. This bore is provided with internal ripples 16 in order to obtain a better grip on said spike. The point of the spike is adapted to pierce the wall 2 closing the bore 15, and liquid can flow off then through lateral apertures towards the bore of the spike.

The neck 10 is intended for adding to the contents of the pouch additional constituents, e.g. medicaments, by means of a hollow needle, e.g. of an injection syringe. For the rest this neck can also be used if drawing-off should be done by means of such a hollow needle. The neck 10 comprises a bore 17 joining, near the flange 11, a wider bore 18, and into the latter a pad 19 of rubber-like material is inserted which can be pierced by the hollow needle, and will seal the hole again when retracting the needle.

As shown the neck axes are inclined at an angle of about 45° in respect of the terminal plane of the flange. Thereby, as clearly appears from FIG. 1, the opposed wall will never be touched when inserting a needle or spike through a neck into the filled pouch 1.

The pouch wall 2 closes the bores of the different necks and thus avoids that the liquid will contact the interior thereof, and in particular the pad 19, and no rubber particles or components thereof can get into the liquid. The wall 2 is pierced when inserting a spike or needle. The bores 15 and 18 of these necks, are, at the other side, closed by a cap 20 with one or more pulling tabs 21, which caps are connected to the neck in question via a tear line, and can be torn off by pulling at the associated tab 21.

The filling tube 13 should connect with the interior of the pouch 1 during filling. This connection is brought about by making, at the location of the spout 8, an incision 23 in the form of a cross in the pouch wall before arranging the assembly 7. This is done when the pouch is flat, using a cutting tool with an accurately adjustable cutting depth, thus avoiding that the opposed pouch wall is damaged. The pointed wall portions set free by the incisions will be pushed away when filling. It is also possible to cut a round hole from the wall, but crossing is simpler and as effective.

Arranging a pad 19 in the neck 10 is very simple, since the enlarged bore 18 immediately joins the flange and its axis is perpendicular to the flange surface so that pressing in a pad is simple. The neck can, for instance, be inserted into a hole in a suitable jig which horizontally supports the flange 11 so that the pad can be pressed with some force tightly into the bore 19. The pouch wall 2 will cover this pad afterwards and provides an additional security. This simple neck shape allows the application of the pad to be mechanised. Another advantage of such a pad which is obliquely directed in respect of the piercing aperture 17 for the needle is that a thinner pad can be used providing, nevertheless, the same contact surface with the needle.

I claim:

1. An infusion liquid pouch comprising:

a tubular pouch closed at both ends and having a planar side wall;

a unitary structure including a pair of hollow necks and a filling tube connector supported by a common flange, said flange having a flange surface attached to said planar pouch wall, at least one of said necks having an enlarged bore portion extending from the flange surface and terminating in a transverse shoulder which is substantially parallel to said flange surface; and a pierceable pad enclosed in said enlarged bore and held against said shoulder only by said planar pouch wall;

said necks and said filling tube connector extending at an angle substantially less than 90 degrees to said flange surface, and said transverse shoulder being substantially parallel to said flange surface such that said pierceable pad is held flat against said planar pouch wall.

2. The pouch of claim 1 wherein said necks and the tube connection are interconnected by means of a relatively stiff connecting ridge forming a part of said unitary structure.

3. The pouch of claim 1 or 2 wherein said filling tube connection comprises a stepped bore.

4. The pouch of claim 1 or 2 wherein said said filling tube connection (13) is a sealed tube section (13).

5. The pouch of claim 1 or 2 wherein at least one said neck is provided with internal ripples.

6. The pouch of claim 1 or claim 2 wherein a throughgoing incision is present in the pouch wall underneath the filling tube connector.

7. The pouch of claim 1 wherein said unitary structure includes removable caps for closing said two necks, said caps being integrally formed with said necks and flange, each of said caps being normally connected to its respective neck by a relatively thin tearoff connection.

8. An infusion liquid pouch comprising:

a tubular pouch closed at both ends and having a planar side wall;

a unitary structure including a pair of hollow necks and a filling tube connector supported by a common relatively rigid flange, each said neck having a closing cap formed integrally therewith, each said cap being connected to its corresponding neck by a tearable portion, said filling tube being closed at its end distal from said flange, said flange having a flange surface attached to said planar pouch wall, at least one of said necks having an enlarged bore portion extending from the flange surface and terminating in a transverse shoulder which is substantially parallel to said flange surface;

a pierceable pad enclosed in said enlarged bore and held against said shoulder only by said planar pouch wall;

said neck and said filling tube connector extending at an angle of substantially less than 90 degrees to said flange surface, said transverse shoulder being substantially parallel to said flange surface such that said pierceable pad is held flat against said planar pouch wall between said flange and said pouch wall.

9. The pouch of claim 1 or claim 8 wherein said necks and said filling tube connector extend at approximately 45 degrees to said flange surface and said transverse shoulder.

* * * * *